(12) United States Patent
Strobl

(10) Patent No.: US 6,498,034 B1
(45) Date of Patent: Dec. 24, 2002

(54) METHOD OF PRODUCING DENDRITIC CELLS

(75) Inventor: Herbert Strobl, Vienna (AT)

(73) Assignee: Novartis AG, Basel (CH)

( * ) Notice: Subject to any disclaimer, the term of this patent is extended or adjusted under 35 U.S.C. 154(b) by 0 days.

(21) Appl. No.: 09/277,668

(22) Filed: Mar. 26, 1999

Related U.S. Application Data

(63) Continuation of application No. 08/909,511, filed on Aug. 12, 1997, now abandoned.

(30) Foreign Application Priority Data

Aug. 14, 1996 (GB) .............................................. 9617058

(51) Int. Cl.$^7$ ................................................ C12N 5/00
(52) U.S. Cl. ........................ 435/325; 435/355; 435/372; 435/377; 435/384; 435/385; 435/387
(58) Field of Search ................................ 435/325, 355, 435/372, 377, 384, 385, 387

(56) References Cited

U.S. PATENT DOCUMENTS 6,004,807 A    12/1999   Banchereau et al. ........ 435/325

OTHER PUBLICATIONS

Mayani et al., Experimental Hematology, 23:422–427, 1995.
Jaffe, Pediatric Pathology, 13:821–837, 1993.
Lardon et al., Experimental Hematology, 22:903–908, 1994.
Snoeck et al., J. Exp. Med., 183:705–710, 1996.
Thomas et al., Stem Cells, 14:196–206, 1996.*
Williams et al., International Review of Cytology, 153:41–103, 1994.*
Strobl et al., TGF–B1 Promotes in Vitro Development Dendritic Cells from CD34+ Hemopoietic Progenitors1, 1996, The Journal of Immunology, vol. 157, pp. 1499–1507.
Inaba et al., J. Exp. Med, vol. 176, "Generation of Large Numbers of Dendritic Cells from Mouse Bone Marrow Cultures Supplemented with Granulocyte/Macrophage Colony–stimulating Factor," pp. 1693–1702 (1992).
Kashihara et al., J. of Investigative Dermatology, vol. 87 (5), "A Monoclonal Antibody Specifically Reactive to Human Langerhans Cells," pp. 602–607 (1986).
Knapp et al., Annals of Hematology, vol. 70, "Molecular characterization of CD34+ human hematopoietic progenitor cells," pp. 281–296 (1995).
Bello–Fernandez C. et al., Human Gene Therapy, vol. 8, "Efficient Retrovirus–Mediated Gene Transfer of Dendritic Cells Generated from CD34+ Cord Blood Cells under Serum–Free Conditions," pp. 1651–1658 (1997).
Bender A. et al., J. of Immunological Methods, vol. 196, "Improved methods for the generation of dendritic cells from nonproliferating progenitors in human blood," pp. 121–135 (1996).

Borkowski T. et al., J. of Experimental Medicine, vol. 184, "A Role for Endogenous Transforming Growth Factor β1 in Langerhans Cell Biology: The Skin of Transforming Growth Factor β1 Null Mice is Devoid of Epidermal Langerhans Cells," pp. 2417–2422 (1996).
Cashman J. et al., Blood, vol. 75, "Mechanisms That Regulates the CellCycle Status of Very Primitive Hematopoietic Cells in Long–Term Human Marrow Cultures. I. Stimulatory Role of a Variety of Mesenchymal Cell Activators and Inhibitory Role of TGF–β," pp. 96–101 (1990).
Caux C. et al., J. Exp. Med., vol. 184, "CD34$^{30}$ Hematopoietic Progenitors from Human Cord Blood Differentiate Along Two Independent Dendritic Cell Pathways in Response to GM–CSF+TNFα," pp. 695–706 (1996).
Caux C. et al., Nature, vol. 360, "GM–CSF and TNF–α cooperate in the generation of dendritic Langerhans cells," pp. 258–261 (1992).
Cruz P. et al., J. of Investigative Dermatology, vol. 92 (2), "Disparate Effects of In Vitro Low–Dose UVB Irradiation on Intravenous Immunization with Purified Epidermal Cell Subpopulations for the Induction of Contact Hypersensitivity," pp. 160–165 (1989).
Enk A. et al., J. of Immunology, vol. 151 (5), "Inhibition of Langerhans Cell Antigen–Presenting Function by IL–10 (A Role for IL–10 in Induction of Tolerance)," pp. 2390–2398 (1993).
Finkelman F. et al., J. of Immunology, "Dendritic Cells Can Present Antigen In Vivo in a Tolerogenic or Immunogenic Fashion," pp. 1406–1414 (1996).
Flores–Romo L. et al., J. Exp. Med., vol. 185(2), "CD40 Ligation on Human Cord Blood CD34$^{30}$ Hematopoietic Progenitors Induces Their Proliferation and Differentiation into Functional Dendritic Cells," pp. 341–349 (1997).
Hatzfeld J. et al., J. Exp. Med., vol. 174, "Release of Early Human Hematopoietic Progenitors from Quiescence by Antisense Transforming Growth Factor β1 or Rb Oligonucleotides," pp. 925–929 (1991).
Imbert A.M. et al., Exp. Hematology, vol. 26, "A neutralizing anti–TGF–β1 antibody promotes proliferation of CD34$^+$Thy–1$^+$ peripheral blood progenitors and increases the number of transduced progenitors," pp. 374–381 (1998).
Lardon F. et al., Exp. Hematology, vol. 22, "Transforming growth factor–β regulates the cell cycle status of interleukin–3 (IL–3) plus IL–1, stem cell factor, or IL–6 stimulated CD34$^+$ human hematopoietic progenitor cells through different cell kinetic mechanisms depending on the applied stimulus," pp. 903–909 (1994).

(List continued on next page.)

Primary Examiner—Leon B. Lankford, Jr.
(74) Attorney, Agent, or Firm—Hesna J. Pfeiffer

(57) ABSTRACT

The present invention relates to a method for producing dendritic cells from human hematopoietic progenitor cells by obtaining a cell sample that includes human progenitor cells and culturing the cell sample under plasma-free and serum-free conditions in the presence of a combination of cytokines to produce dendritic cells, where the combination of cytokines include TGF-β1.

4 Claims, 8 Drawing Sheets

OTHER PUBLICATIONS

Figure 6A:
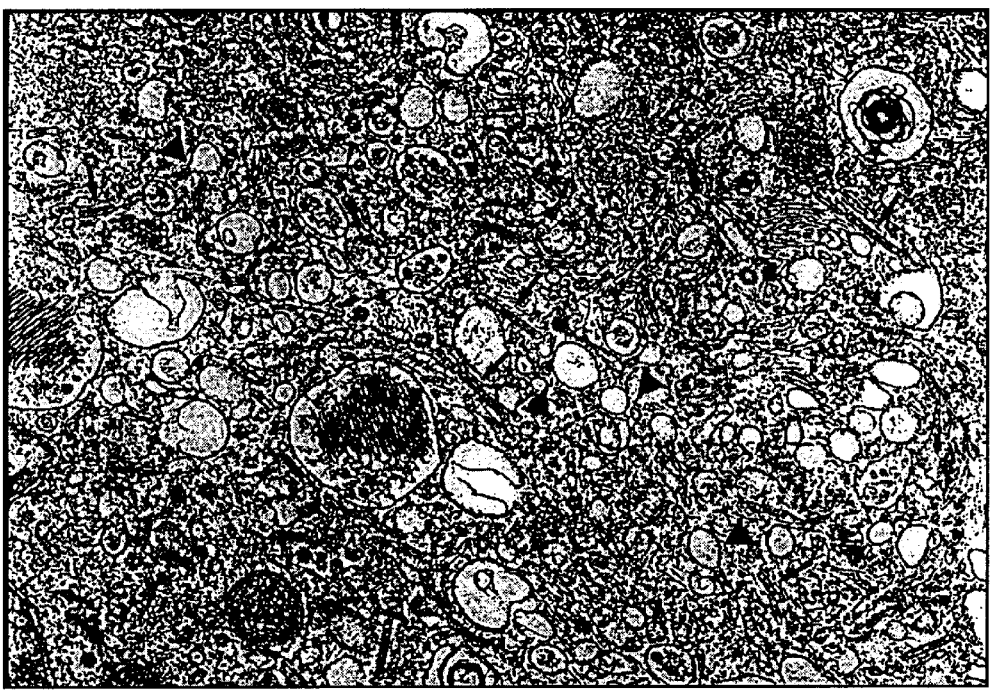

Lu L. et al., Experimental Hematology, vol. 21, "Comparative effects of suppressive cytokines on isolated single CD34+++ stem/progenitor cells from human bone marrow and umbilical cord blood plated with and without serum," pp. 1442–1446 (1993).

Reid C. et al., J. of Immunology, vol. 149 (8), "Interactions of Tumor Necrosis Factor with Granulocyte–Macrophage Colony–Stimulating Factor and Other Cytokines in the Regulation of Dendritic Cell Growth In Vitro from Early Bipotent CD34+ Progenitors in Human Bone Marrow," pp. 2681–2688 (1992).

Riedl E. et al., J. of Immunology, vol. 158, "TGF–β1 Promotes In Vitro Generation of Dendritic Cells by Protecting Progenitor Cells from Apoptosis," pp. 1591–1597 (1997).

Roman N. et al., J. of Immunological Methods, vol. 196, "Genration of mature dendritic cells from human blood: An improved method with special regard to clinical applicability," pp. 137–151 (1996).

Sauder D. et al., J. of Immunology, vol. 127 (1), "Induction of Tolerance to Topically Applied TNCB Using TNP–Conjugated Ultraviolet Light–Irradiated Epidermal Cells," pp. 261–265 (1981).

Siena S. et al., Experimental Hematology, vol. 23, "Massive ex vivo generation of functional dendritic cells from mobilized CD34+ blood progenitors for anticancer therapy," pp. 1463–1471 (1995).

Simon J. et al., J. of Immunology, vol. 146 (2), "Ultraviolet B Radiation Converts Langerhans Cells from Immunogenic Antigen–Presenting Cells," pp. 485–491 (1991).

Steinman R., Annu. Rev. Immunol., vol. 9, "The Dendritic Cell System and its Role in Immunogenicity," pp. 271–296 (1991).

Steinman R. et al., J. Invest Dermatol., vol. 105 (1) [Supplement], "Maturation and Migration of Cutaneous Dendritic Cels," pp. 2S–7S (1995).

Steptoe R.J. and Thomson A. W., Clin. and Exp. Immunol., vol. 105, "Dendritic cells and tolerance induction," pp. 397–402 (1996).

Strobl H. et al., Blood, vol. 90 (4), "flt3 Ligand in Cooperation with Transforming Growth Factor β–1 Potentiates In Vitro Development of Langerhans–Type Dendritic Cells and Allows Single–Cell Dendritic Cell Cluster Formation Under Serum–Free Conditions," pp. 1–10 (1997).

Strobl H. et al., J. Immunol., vol. 157, "TGF–β1 Promotes In Vitro Development of Dendritic Cells from CD34° Hemopoietic Progenitors," pp. 1499–1507 (1996).

Strobl H. et al., Immunobiology, vol. 198, "Epidermal Langerhans Cell Development and Differentation," pp. 588–605 (1997/1998).

Szabolcs P. et al., J. Immunol., "Expansion of Immunostimulatory Dendritic Cells Among the Myeloid Progeny of Human CD34+ Bone Marrow Precursors Cultured with c–*kit* Ligand, Granulocyte–Macrophage Colony–Stimulating Factor, and TNF–α," pp. 5851–5860 (1995).

Young J. et al., J. Exp. Med., vol. 182, "Identification of Dendritic Cell Colony–forming Units among Normal Human CD34+ Bone Marrow Progenitors That Are Expandedby c–*kit*–ligand and Yield Pure Dendritic Cell Colonies in the Presence of Granulocyte/Macrophage Colony–stimulating Factor and Tumor Necrosis Factor α," pp. 1111–1120 (1995).

Yu J. et al., Gene Therapy, vol. 5, "Abrogation of TGF–β activity during retroviral transduction improves murine hematopoietic progenitor and repopulating cell gene transer efficiency," pp. 1265–1271 (1998).

* cited by examiner

FIGURE 1. Generation of CD1a+ cells in the presence of cord blood plasma.

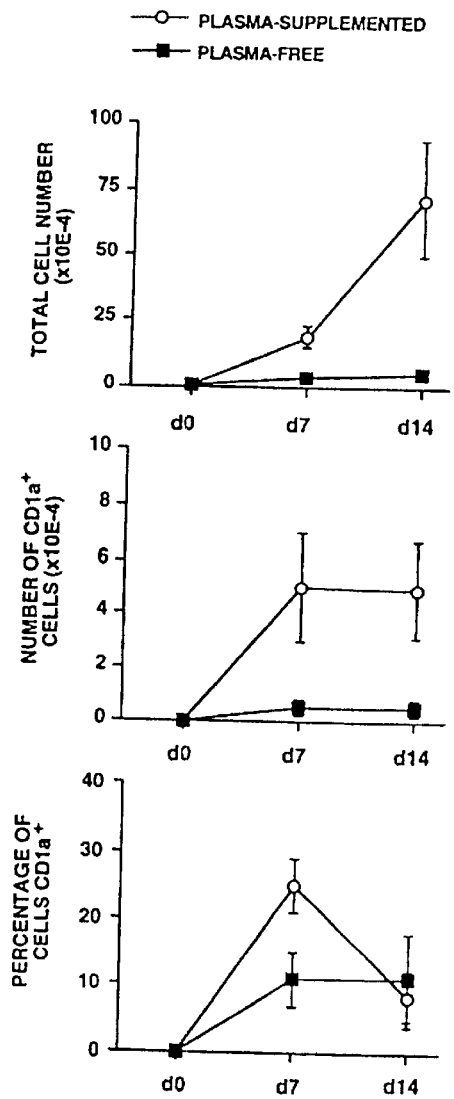

CD34+ cells purified from umbilical cord blood (CB) were cultured in GM-CSF+TNFα+SCF supplemented medium in the presence or absence of 10% cord blood plasma as described. Total cell numbers (top), numbers of CD1a+ cells (center) and percentages of CD1a+ cells (bottom) observed at days 7 and 14 of culture are shown. The number of CD1a+ cells was calculated from the percentage of CD1a+ cells multiplied by the total number of cells in each culture. Each value represents the mean±SEM of 4 experiments.

FIGURE 2. The effects of TGF-β1 addition to plasma-free cultures.

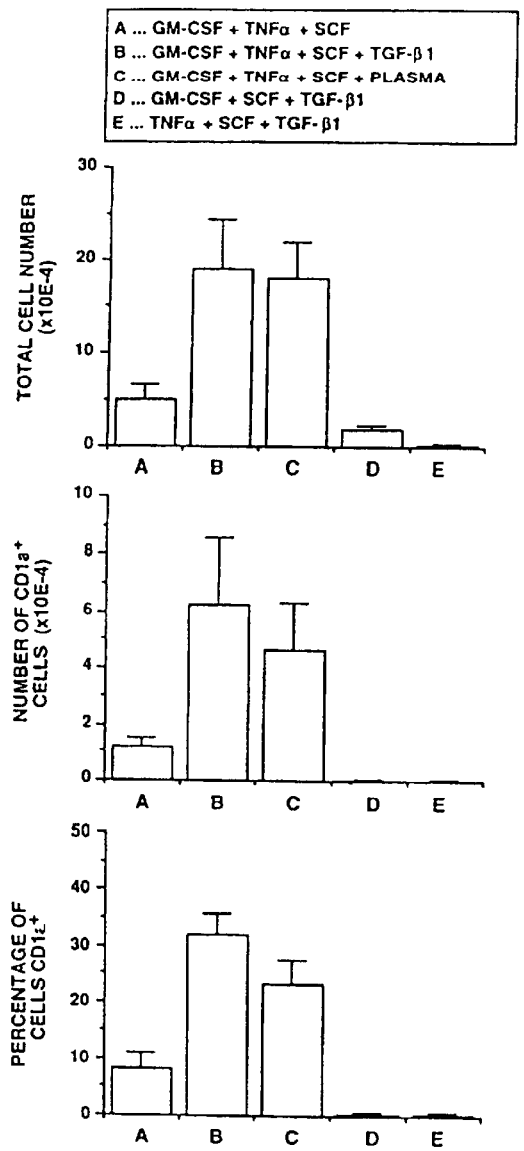

CD34+ CB cells were cultured for 7 days in cytokine supplemented plasma-free medium as described. Cultures were supplemented with optimized concentrations of the indicated cytokines, with or without 0.5 ng/ml TGF-β1 or 10% cord blood plasma (as indicated in the Figure). Bars represent mean±SEM of total cell numbers (top), numbers of CD1a+ cells (center) or percentages of cells positive for CD1a expression (bottom) observed in 5 experiments. The number of CD1a+ cells was calculated from the percentage of CD1a+ cells multiplied by the total number of cells in each culture.

FIGURE 3. Concentration dependent enhancement of cell proliferation and generation of CD1a+ cells in plasma free cultures in the presence of TGF-β1.

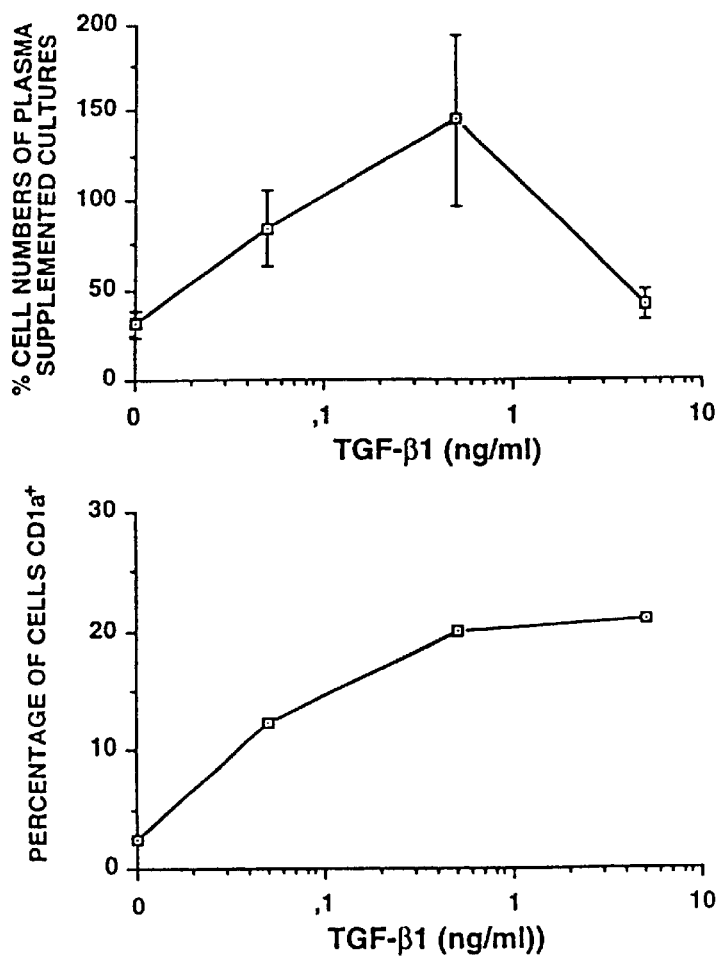

CD34+ CB cells were cultured for 7 days in GM-CSF+TNFα+SCF supplemented plasma-free medium as described. Upper diagram: Mean±SEM of cell numbers observed in 3 experiments. Cell numbers are normalized to those observed in plasma-supplemented TGF-β1-free parallel cultures. Lower diagram: Percent CD1a+ cells observed in plasma-free cultures supplemented with GM-CSF+TNFα+SCF and variing concentrations of TGF-β1.

FIGURE 4. Microscopic appearance of 10-day cultures.
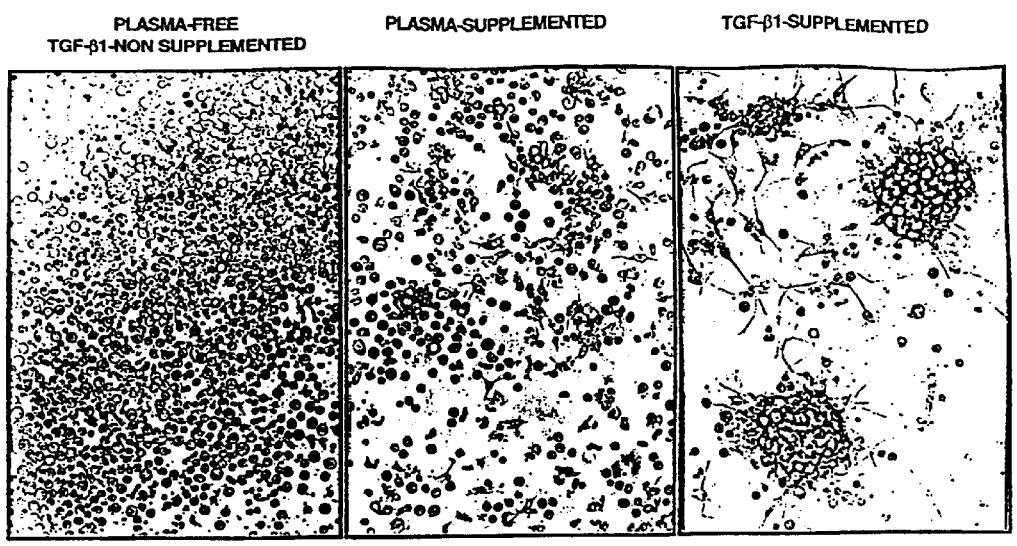
CD34+ CB cells were cultured in GM-CSF+TNFα+SCF supplemented plasma-free medium (left), or with additional supplementation with 10% cord blood plasma (center) or 0.5 ng/ml TGF-β1 (right).

FIGURE 5. Analysis of Lag expression by cultured cells.

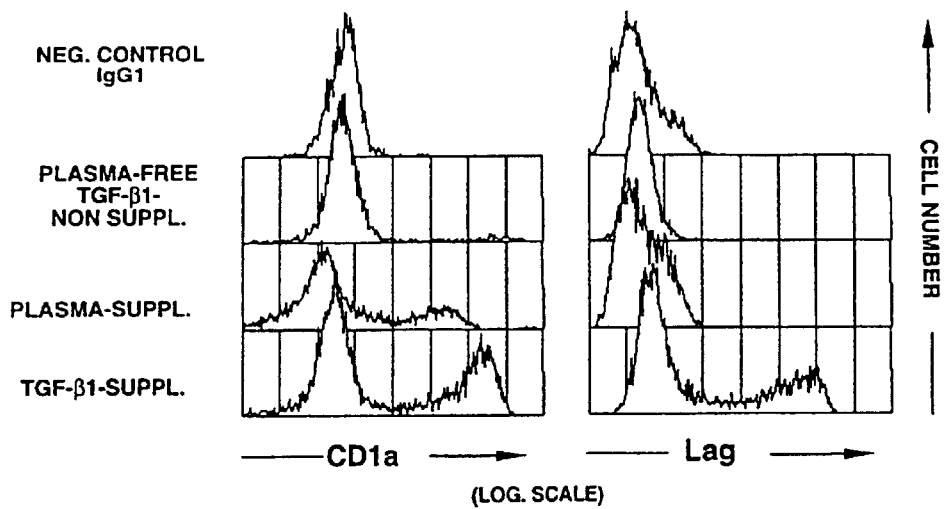

CD34+ CB cells were cultured for 10 days in GM-CSF+TNFα+SCF supplemented plasma-free suspension cultures as described. Parallel cultures were additionally supplemented with either 0.5 ng/ml TGF-β1 or 10% cord blood plasma. Cells were stained for CD1a or intracellular Lag expression as described. Representative histograms show cells analyzed in parallel for Lag or CD1a expression.

FIGURE 6.

Figure 6B:
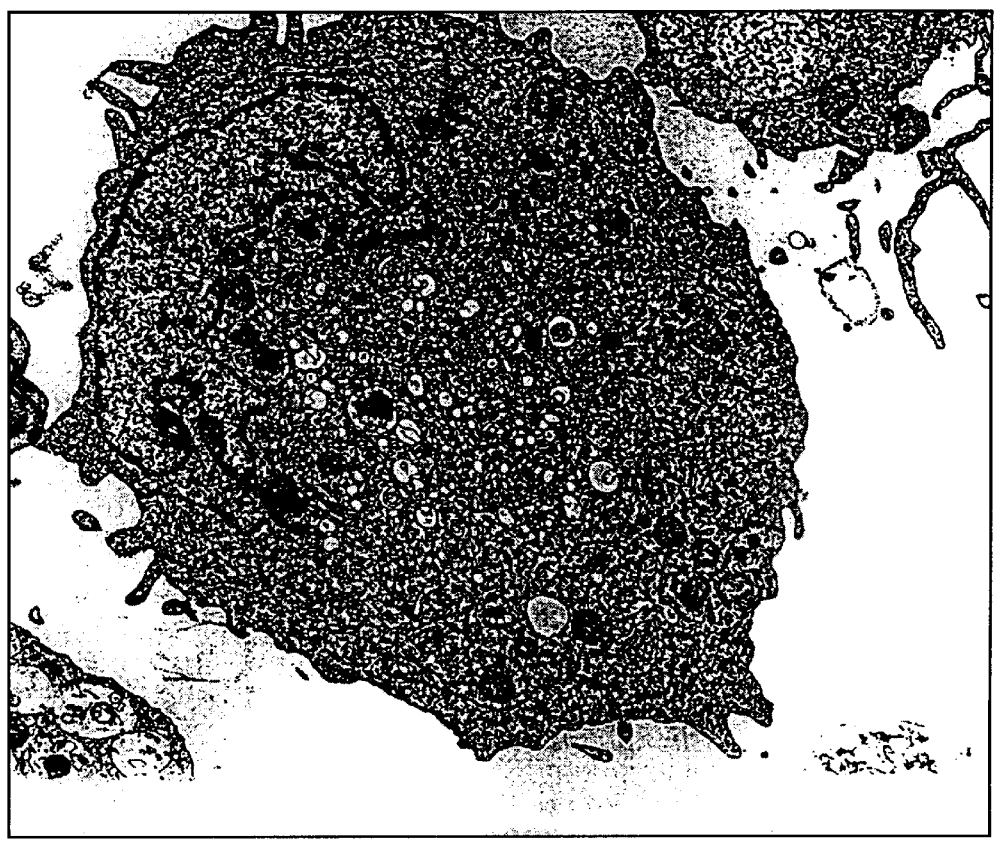

In vitro-generated dendritic cells display characteristic ultrastructural features of epidermal Langerhans cells in vivo. This representative cell displays a roundish shape and shows several villous projections protruding from the cell membrane. The nucleus is eccentrically localized and has a characteristic indented and even lobulated structure. Within the cytoplasm are numerous organelles that morphologically define Langerhans cells, the Langerhans cell/Birbeck granules with their characteristic rod or racket-shape. In vitro-generated dendritic cells contain numerous such granules within their cytoplasm. Arrows indicate rod-shaped Langerhans cell granules; arrowheads indicate racket-shaped Langerhans cell granules; stars indicate lamellar bodies. Magnification: x12,000 (Fig. 6A ); x36,000 (Fig. 6B).

FIGURE 7. MLR-stimulatory capacity of cells generated in the presence of TGF-β1.

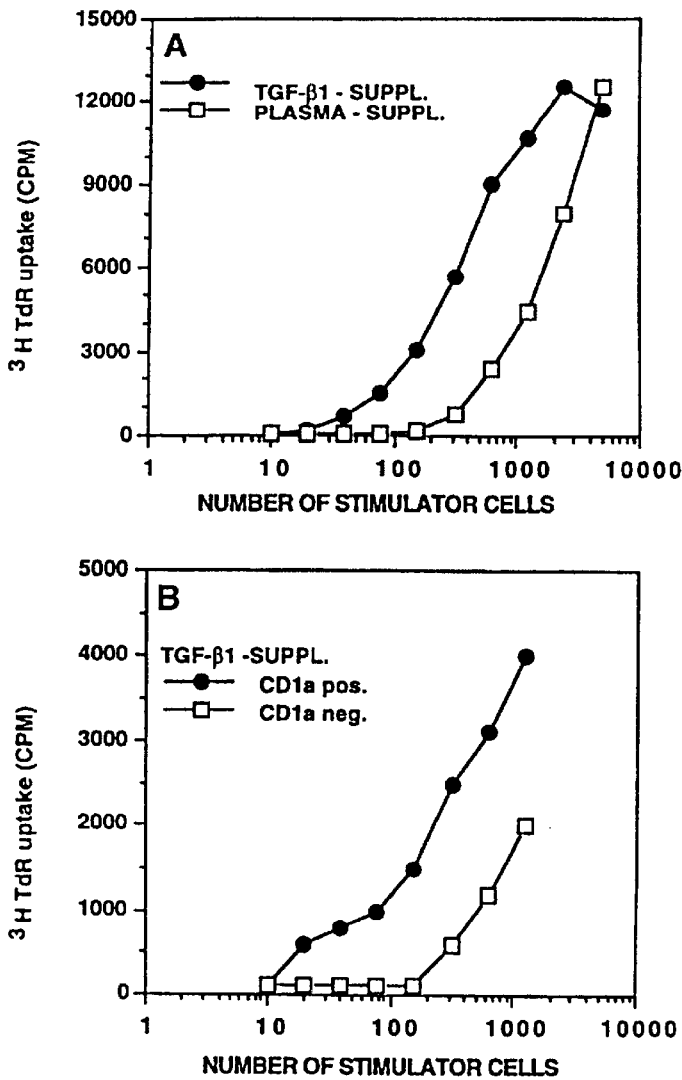

CD34+ CB cells were cultured for 10 days in GM-CSF + TNF-α + SCF-supplemented plasma-free suspension cultures. Parallel cultures were additionally supplemented with either 0.5 ng/ml TGF-β1 or 10 % CB as indicated. Graded numbers of in vitro-generated cells, after remaining in culture for 10 days, were used to stimulate $10^5$-purified allogeneic T cells.

A. Unfractionated cultured cells used as stimulator cells. Values are representative of three independent experiments.

B. TGF-β1-supplemented cultures fractionated into CD1a⁻ and CD1a⁻ cell populations by flow sorting.

METHOD OF PRODUCING DENDRITIC CELLS

This application is a continuation of application Ser. No. 08/909,511, filed Aug. 12, 1997, now abandoned.

BACKGROUND OF THE INVENTION

Substantial numbers of functional dentritic cells (DC) can be generated from precursor cells in blood or bone marrow upon in vitro culture with appropriate combinations of cytokines. For the in vitro development of DC from human $CD34^+$ progenitor cells the most efficient cytokine combination was found to be GM-CSF plus TNFα and SCF. The culture media used for growing functional DC from progenitor cells were not only supplemented with exogenous cytokines, however, but also with serum or plasma. This raised the question whether, in addition to the added cytokines, also as yet undefined serum components play a critical role in the in vitro DC development. TGF-β1, known to be present in serum and plasma samples, is such a component. In its presence, but not or only minimally in its absence can substantial numbers of DC be generated from $CD34^+$ progenitor cells also under serum/plasma-free conditions.

SUMMARY OF THE INVENTION

The invention concerns a process for the production of DC under serum/plasma-free conditions in the presence of TGF-β1.

BRIEF DESCRIPTION OF THE PREFERRED EMBODIMENTS

TGF-β1 plays a critical role in the in vitro development of dendritic cells from hemopoietic progenitor cells under serum-free culture conditions. Addition of TGF-β1 to the culture medium replaces the requirement of plasma-supplementation for the cytokine dependent generation of high numbers of DC from purified $CD34^+$ cord blood progenitor cells. The basic cytokine combination of GM-CSF plus TNFα and SCF in the absence of either plasma or TGF-β1 induces only low percentages and low total yields of $CD1a^+$ DC (see FIG. 1). Addition of plasma or TGF-β1 to this basic cytokine combination, however, strongly induces cell proliferation and differentiation of $CD1a^+$ DC within a culture period of 7 to 10 days (see FIG. 2).

Quantitatively; TGF-β1 does not just complement the effect of plasma in the efficiency to generate DC. At day 10, TGF-β1-supplemented cultures contain even higher absolute numbers of $CD1a^+$ DC, and at an even higher percentage than plasma-supplemented cultures. TGF-β1-supplemented cultures differ from plasma-supplemented cultures in several aspects. Firstly, large cell aggregates are only observed in TGF-β1-supplemented cultures (FIG. 4). Secondly only TGF-β1-supplemented cultures contain cells positive for the Langerhans cell Birbeck granule antigen Lag (FIG. 5) and possess numerous typical cytoplasmic Langerhans cell/Birbeck granules (FIG. 6). Finally, cells from TGF-β1-supplemented cultures are more potent inducers of an allogeneic mixed leukocyte reaction (MLR) than cells from plasma-supplemented parallel cultures (FIG. 7).

Mature dendritic cells occur as trace cell populations in many tissues and blood. The isolation of these cells is, however, complicated by low cell purities and yields. Therefore recently interest focused on the in vitro generation of DC from hemopoietic progenitor cells. It was found, that the two cytokines GM-CSF and TNFα are in principle sufficient for the in vitro generation of DC, and that addition of SCF further boosts DC recovery. In all these processes, serum-containing culture medium was used, however. In vitro generation of DC in the absence of serum supplementation gives significantly lower DC recoveries. Therefore, undefined serum components including cytokines known to be present in serum obviously play a role in development of DC in vitro.

One of the cytokines known to be present in serum and plasma in substantial amounts is TGF-β1. TGF-β1 is a pleiotropic 25-kD homodimeric polypeptide produced by many different cell types and with a variety of biological activities including the stimulation of cell proliferation and differentiation of many cell types. TGF-β1 belongs to a superfamily of evolutionarily highly conserved regulatory proteins. Three isoforms of TGF-β are expressed in mammals (TGF-β1, 2 and 3), and those share sequence homology in the bioactive domain. TGF-β1, a prototype of this family generates most of the biological actions of the others. Its action on hemopoietic progenitor cells has been extensively studied in vitro. Previous studies demonstrated that the effects of TGF-β on hemopoietic progenitor cells seem largely to depend upon the state of differentiation of these cells, and the presence or absence of other growth factors. On immature progenitor cells TGF-β exerts mainly inhibitory effects. TGF-β inhibits cycling of primitive stroma-dependent long-term culture-initiating cells (LTC-IC), reduces the number of high-proliferative-potential colony-forming cells (HPP-CFC) and inhibits the expansion of immature $CD38^-CD34^+$ or $CD34^{bright}$ progenitor cells in suspension cultures. This negative effect on cell proliferation seems to be directly mediated by TGF-β and occurs within 48 hours of stimulation.

In contrast, on more mature, lineage committed progenitor cells, and in the presence of certain cytokines such as GM-CSF, macrophage colony-stimulating factor (M-CSF), or erythropoietin plus Interleukin 3 and SCF, co-stimulatory effects of TGF-(3 were also described, on cell proliferation and/or differentiation. In particular, during macrophage differentiation, autocrine production of TGF-β seems to contribute to growth factor dependent proliferation.

The here described stimulatory effect of TGF-β1 is strictly dependent upon the simultaneous presence of GM-CSF and TNFA, since no or only minimal cell expansion and DC differentiation is observed upon addition of TGF-β1 to combinations of either SCF plus GM-CSF or SOF plus TNFα. Thus, TGF-β1 seems to specifically act together with GM-CSF plus TNFA which represent a strong stimulus for the proliferation and differentiation of myeloid cells and DC.

One important finding of the present invention is the selective induction of cells with highly immunostimulatory capacity (FIG. 7), strong CD1a expression, and Lag reactivity in TGF-β1-supplemented cultures (FIG. 5). Lag antigen represents a 40-kDa glycoprotein which is associated with Birbeck granules and which shows specificity for epidermal Langerhans cells and DC populations from lymph nodes and thymus. Strikingly, in contrast to CD1a expression, we never observed Lag reactive cells in parallel cultures without TGF-β1-supplementation or with plasma-supplementation (see FIG. 5). This suggests that TGF-β1 induces a population with specific features of differentiated DC. In line with this, Lag reactivity occurs relatively late during culture (day 10) and correlates with the appearance of cells with highly dendritic morphology (see FIG. 4). Previous studies failed to generate large proportions of Lag reactive cells from $CD34^+$ progenitor cells in vitro.

In the following examples which illustrates the invention without limiting it, all temperatures are in degree Celsius. The following abbreviations are used:

| | |
|---|---|
| DC | dendritic cells |
| GM-CSF | granulocyte-macrophage colony stimulativ factor |
| TNFα | tumor necrosis factor α |
| SCF | stem cell factor |
| TGF-β1 | transforming growth factor β1 |
| MLR | mixed leukocyte reaction |
| LTC-IC | long term culture initiating cells |
| HPP-CFC | high proliferative potential colony forming cells |
| M-CSF | macrophage colony stimulating factor |
| PBS | phosphate buffered saline |
| FACS | fluorescence activated cell sorting |
| CB | cord blood |
| MNC | mononuclear cells |
| CBPI | cord blood plasma |

Immunofluorescence Staining Procedures

For membrane staining, 50 µl of isolated mononuclear cells (MNC; $10^7$/ml) were incubated for 15 minutes at 0° C.–4° C. with 20 µl of conjugated monoclonal antibody. For suspension stainings of the intracellular antigens, we used the commercially available reagent combination Fix&Perm from An der Grub according to the manufacturer's procedure. In short, cells are first fixed for 15 minutes at room temperature (50 µl of cells plus 100 µl of formaldehyde based Fixation Medium). After one washing with PBS pH 7.2 (PBS), cells are resuspended in 50 µl of PBS and mixed with 100 µl of Permeabilization Medium plus 20 µl of fluorochrome labeled antibody. After a further incubation for 15 minutes at room temperature, cells are washed again and analyzed by flow cytometry.

Flow Cytometry

Flow cytometric analyses were performed using a FACScan flow cytometer equipped with a single laser emitting at 488 nm. $CD1a^+$ and $CD1a^-$ cell fractions were obtained by flow sorting using a FACS Vantage flow cytometer (Becton Dickinson). The purity of the fractions obtained by sorting was determined by reanalysis and found to be greater than 95%.

Cord Blood Cells

Cord blood (CB) samples were collected during normal full-term deliveries. MNC were isolated within 10 hours after collection using discontinuous Ficoll/Hypaque density gradient centrifugation. $CD34^+$ cells were isolated from CB MNC using the MACS CD34 Progenitor Cell Isolation Kit, according to the instructions of the manufacturer. The purity of the $CD34^+$ population ranged from 87% to 98% (mean =94%).

Cultivation of $CD34^+$ CB Cells

Culture of purified $CD34^+$ CB cells was performed in 24 well plates ($1-3 \times 10^4$ cells in 1 ml/well) at 37° C. in a humidified atmosphere and in the presence of 5% $CO_2$. The serum-free medium X-VIVO 15 (Bio Whittaker, Walkersville, Md.) contained L-glutamine (2.5 mM), penicillin (125 IE/ml) and streptomycin (125 µg/ml). Cultures were supplemented with optimized concentrations of the following human cytokines: TGF-β1 (0,5 ng/ml), rhTNFα (50 U/ml), rhGM-CSF (100 ng/ml) and rhSCF (20 ng/ml). When indicated, serum-free cultures were supplemented with 10% pooled human umbilical cord blood plasma (CBPI) obtained from at least three individuals. Identical cell multiplication and differentiation patterns were observed in cultures initiated with $1 \times 10^4 - 3 \times 10^4$ purified $CD34^+$ cells. Therefore, all cell numbers presented are normalized to $1 \times 10^4$ purified $CD34^+$ cells seeded at culture initiation.

Mixed Leucocyte Reactions (MLR)

Freshly isolated or cultured cell fractions were irradiated with 30 Gy ($[^{137}Cs]$ source). Subsequently, graded numbers of these stimulator cells were mixed with a constant amount ($5 \times 10^4$) of highly purified peripheral blood T cells and seeded into round-bottomed 96-well tissue culture plates. T cells were prepared by paramagnetic depletion for non-T cells. Purity, as determined by FACS analysis proved to be greater than 98%. Stimulation of responding T cells was monitored by measuring methyl-$[^3H]$-thymidine incorporation into newly synthesized DNA on day 5 of culture. The incorporated radioactivity was measured by a Top-Count microscintillation counter.

Ultrastructural Analysis of in Vitro Generated Cells

Transmission electron microscopy was performed as described. Briefly, cultured cells ($1 \times 10^6$) were harvested, washed twice in PBS and once in 0.1 mol/L cacodylate buffer and fixed for 30 minutes in 2.5% glutaraldehyde and 2% paraformaldehyde (pH=7.2). After fixation, cells were postfixed in 4% OSO4 for 1 hour at room temperature, dehydrated in a graded series of ethanol, and infiltrated with and polymerized in EPON 812. Thin sections were stained with uranyl-acetate and lead citrate on a grid and examined by transmission electron microscopy.

Plasma Supplementation of Culture Medium is Required for the Efficient in Vitro Development of DC In accordance with the state of the art on in vitro DC generation in serum-containing medium we could generate substantial numbers of $CD1a^+$ cells upon culture of purified $CD34^+$ progenitors with cord blood plasma (10%) containing culture medium supplemented with the cytokines GM-CSF, TNFα and SCF (FIG. 1). The total number of cells increased from $1 \times 10^4$ to $69 \pm 22 \times 10^4$. The proportion of cells expressing the DC marker molecule CD1a increased from 0% at day 0 to $25 \pm 4\%$ at day 7 and $8 \pm 4\%$ at day 14. Omission of plasma from the culture medium dramatically reduced both the total number of recovered cells and the proportion of $CD1a^+$ cells (FIG. 1). In fact, as shown in FIG. 1, in the absence of plasma, hardly any proliferation occured. The total number of $CD1a^+$ cells recovered dropped at day 7 from $5 \pm 2 \times 10^4$, in the presence of plasma, to $0.5 \pm 0.2 \times 10^4$ in its absence and at day 14 from $5 \pm 2 \times 10^4$ to $0.5 \pm 0.3 \times 10^4$.

Supplementation of Plasma-free Culture Medium with TGF-1 Strongly Enhances DC Development As shown in FIG. 2, addition of TGF-β1 to GM-CSF plus TNFα and SCF supplemented plasma-free culture medium significantly enhances both total cell growth and the development of $CD1a^+$ cells. Total cell recovery and the recovery of $CD1a^+$ cells upon culture with TGF-β1-supplemented medium are, in fact, equivalent to the respective recoveries upon culture with plasma-supplemented medium (FIG. 2; values expressed in bars A are significantly lower than those expressed in bars B and C, respectively; $p<0.05$; Student's t test).

Titration experiments revealed that 0.5 ng/ml TGF-β1 give optimal results. At higher concentrations, the proportions of CD1a$^+$ cells stay constant, but total cell recovery drops (FIG. 3).

Also in TGF-β1-supplemented cultures, the addition of GM-CSF plus TNFα is required. Both total cell numbers and proportions of CD1a positive cells drop significantly, when either of the two cytokines is omitted (FIG. 2).

Morphological Analysis of in Vitro Generated DC

The morphological appearances of cells grown in either culture medium alone, plasma-supplemented culture medium or TGF-β1-supplemented culture medium, each in the presence of GM-CSF plus TNFA and SCF, were strikingly different (FIG. 4). Cells grown in plasma- and TGF-β1-free culture medium were round shaped, devoid of cells with dendritic morphology and contained very few small aggregates. Cultures with plasma-supplemented medium were composed mainly of small dendritic cell clusters and of adherent macrophage-type cells. On the other hand, TGF-β1-supplemented cultures, contain large aggregates consisting of most of the cells present in the culture. Loosely adherent to these aggregates, cells with highly dendritic morphology predominate.

What is claimed is:

1. A method for preparing CD1a-positive and Lag reactive dendritic cells (DC) from human progenitor cells comprising the steps of:

isolating a cell sample comprising human CD34-positive hematopoietic progenitor cells;

and culturing at least one cell of the cell sample under plasma-free and serum-free conditions in the presence of a combination of cytokines comprising GM-CSF, TNFα and TGF-β1 to generate CD1a-positive and Lag reactive dendritic cells.

2. The method of claim 1, wherein the combination of cytokines further comprises SCF.

3. The method of claim 2, wherein the CD1a-positive and Lag reactive dendritic cells generated in the presence of TGF-β1 have increased CD1a-expression and Lag-reactivity as compared with dendritic cells generated in the absence of TGF-β1.

4. The method of claim 2 wherein CD1a-positive and Lag reactive dendritic cells generated in the presence of TGF-β1 have increased immunostimulatory capacity as compared with dendritic cells generated in the absence of TGF-β1.

* * * * *